US00PP12765P2

(12) United States Plant Patent
Cleveland

(10) Patent No.: US PP12,765 P2
(45) Date of Patent: Jul. 9, 2002

(54) GINKGO TREE NAMED 'GOLDEN GLOBE'

(75) Inventor: David Hendricks Cleveland, Fort Valley, GA (US)

(73) Assignee: Cleveland Tree Company, Fort Valley, GA (US)

( * ) Notice: Subject to any disclaimer, the term of this patent is extended or adjusted under 35 U.S.C. 154(b) by 25 days.

(21) Appl. No.: 09/738,910

(22) Filed: Dec. 18, 2000

(51) Int. Cl.[7] ..... A01H 5/00
(52) U.S. Cl. ..... Plt./216
(58) Field of Search ..... Plt./216, 213, 215

*Primary Examiner*—Bruce R. Campell
*Assistant Examiner*—June Hwu
(74) *Attorney, Agent, or Firm*—C. A. Whealy

(57) ABSTRACT

A new and distinct cultivar of Ginkgo tree named 'Golden Globe', characterized by its globose and rounded plant shape; very freely branching, high branching density; rapid growth rate; and bright yellow-colored leaves in the autumn.

2 Drawing Sheets

BACKGROUND OF THE INVENTION

The present Invention relates to a new and distinct cultivar of Ginkgo tree, botanically known as *Ginkgo biloba*, and hereinafter referred to by the name 'Golden Globe'.

The new Ginkgo was discovered by the Inventor in a controlled environment in Fort Valley, Ga., during the summer of 1992 as a chance seedling of two unidentified selections of *Ginkgo biloba*.

Asexual reproduction of the new Ginkgo by cuttings in a controlled environment in Fort Valley, Ga. since 1992, has shown that the unique features of this new Ginkgo are stable and reproduced true to type in successive generations.

SUMMARY OF THE INVENTION

The cultivar 'Golden Globe' has not been observed under all possible environmental conditions. The phenotype may vary somewhat with variations in environment such as temperature, daylength, light intensity, and water and nutritional status without, however, any variance in genotype.

The following traits have been repeatedly observed and are determined to be the unique characteristics of 'Golden Globe'. These characteristics in combination distinguish 'Golden Globe' as a new and distinct Ginkgo:

1. Globose and rounded plant shape.
2. Very freely branching, high branching density.
3. Rapid growth rate.
4. Bright yellow-colored leaves in the autumn.

In side-by-side comparisons conducted by the Inventor in Fort Valley, Ga., trees of the new Ginkgo differ from trees of other Gingko cultivars known to the Inventor primarily in plant shape and branching density.

BRIEF DESCRIPTION OF THE PHOTOGRAPHS

The accompanying colored photographs illustrate the overall appearance of the new Ginkgo, showing the colors as true as it is reasonably possible to obtain in colored reproductions of this type. Colors in the photographs may differ slightly from the color values cited in the detailed botanical description which accurately describe the colors of the new Ginkgo.

The photograph on the first sheet comprises a side perspective view of a typical tree of 'Golden Globe', 30 years old during the autumn.

The photograph on the second sheet is a close-up view of a typical tree of 'Golden Globe' during the winter showing the branching density.

DETAILED BOTANICAL DESCRIPTION

In the following description, color references are made to The Royal Horticultural Society Colour Chart except where general terms of ordinary dictionary significance are used. The following observations and measurements describe trees grown in Fort Valley, Ga., under commercial practice in a outdoor field nursery. Trees measured were about 6 years from planting.

Botanical classification: *Ginkgo biloba* cultivar Golden Globe.

Parentage: Seedling of two unidentified selections of *Ginkgo biloba*, not patented.

Propagation:

*Type.*—Softwood cuttings.

*Time to develop roots.*—About 18 months are required before young plants are planted into a field nursery.

*Root description.*—Fleshy, coarse.

Plant description:

*Plant form.*—Upright, globose and rounded tree.

*Branching habit.*—Freely branching, dense; about 18 secondary branches from the first five scaffold branches; and about 7.8 branches per 50 cm of stem length. Angle of attachment, about 38° from vertical. Excellent stem strength.

*Growth rate.*—About 30 to 60 cm per year.

*Plant height.*—About 3.35 meters.

*Plant width.*—About 3.37 meters.

*Stem color.*—First year shoots, 199B; older woody stems, gray, close to 198B.

*Trunk texture.*—Ridged and furrowed.

*Winter leaf buds.*—Imbricate often acute and brownish in color.

*Leaves.*—Arrangement: Simple, alternate. Length: About 9.5 cm. Width: About 9.9 cm. Shape: Fan-shaped to obcordate. Apex: Rounded. Base: Cuneate. Margin: Entire or emarginate; undulate. Texture:

Glabrous; rough. Petiole length: About 5.6 cm. Petiole diameter: About 1.5 mm. Color: Young leaves, upper surface: 138A. Young leaves, lower surface: 138A. Mature leaves, upper surface: 143A; autumn color, 13A. Mature leaves, lower surface: 139B. Petiole: 141C.

Reproductive structures description:

*Habit.*—Only male structures observed. Single reproductive structures, male, catkin-like. Not fragrant. Not persistent.

*Natural maturation season.*—Male reproductive structures mature in late March to early April in Fort Valley, Ga.

*Size.*—Length: About 1.1 cm. Diameter: About 5 mm.

*Seed.*—Seed production has not been observed.

Disease resistance: Resistance to pathogens common to Ginkgo has not been determined.

It is claimed:

1. A new and distinct cultivar of Ginkgo tree named 'Golden Globe', as illustrated and described.

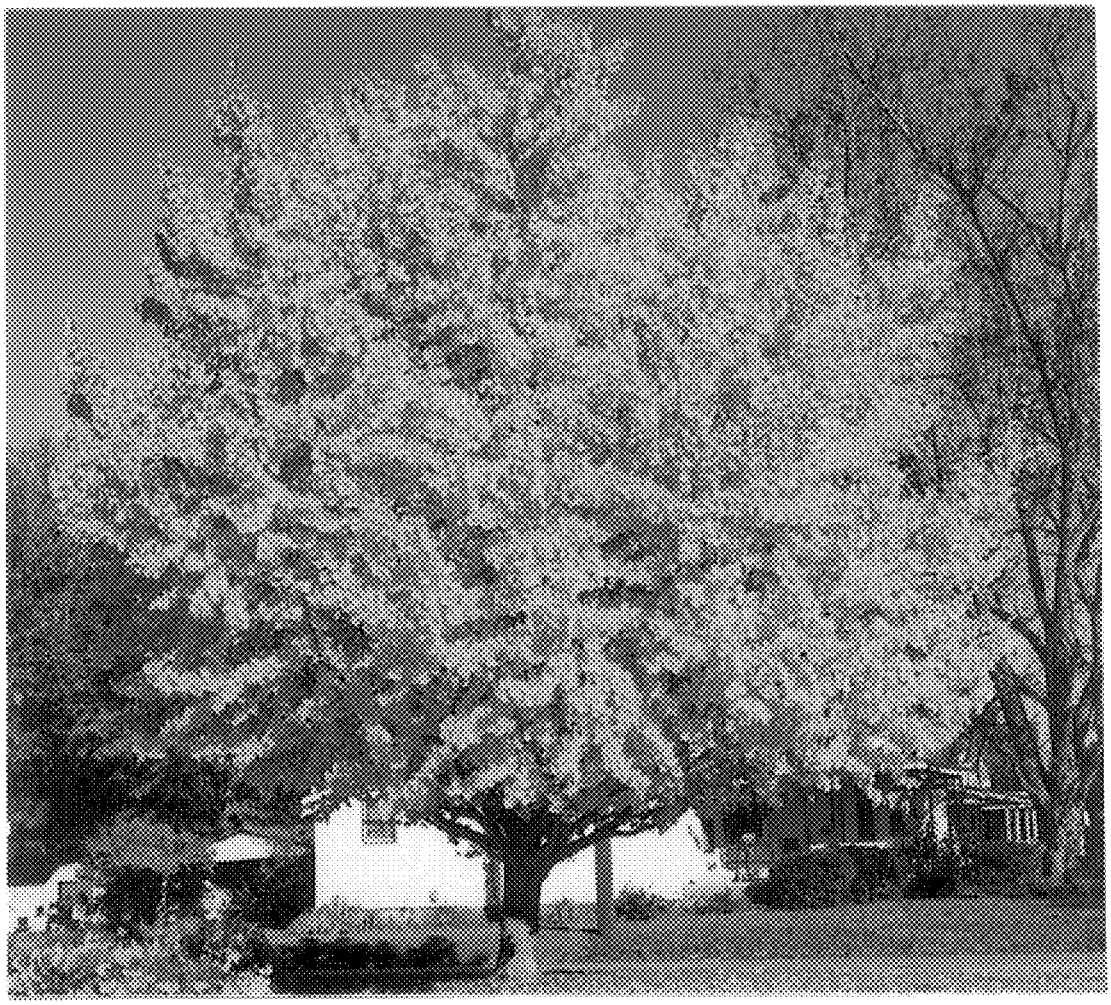

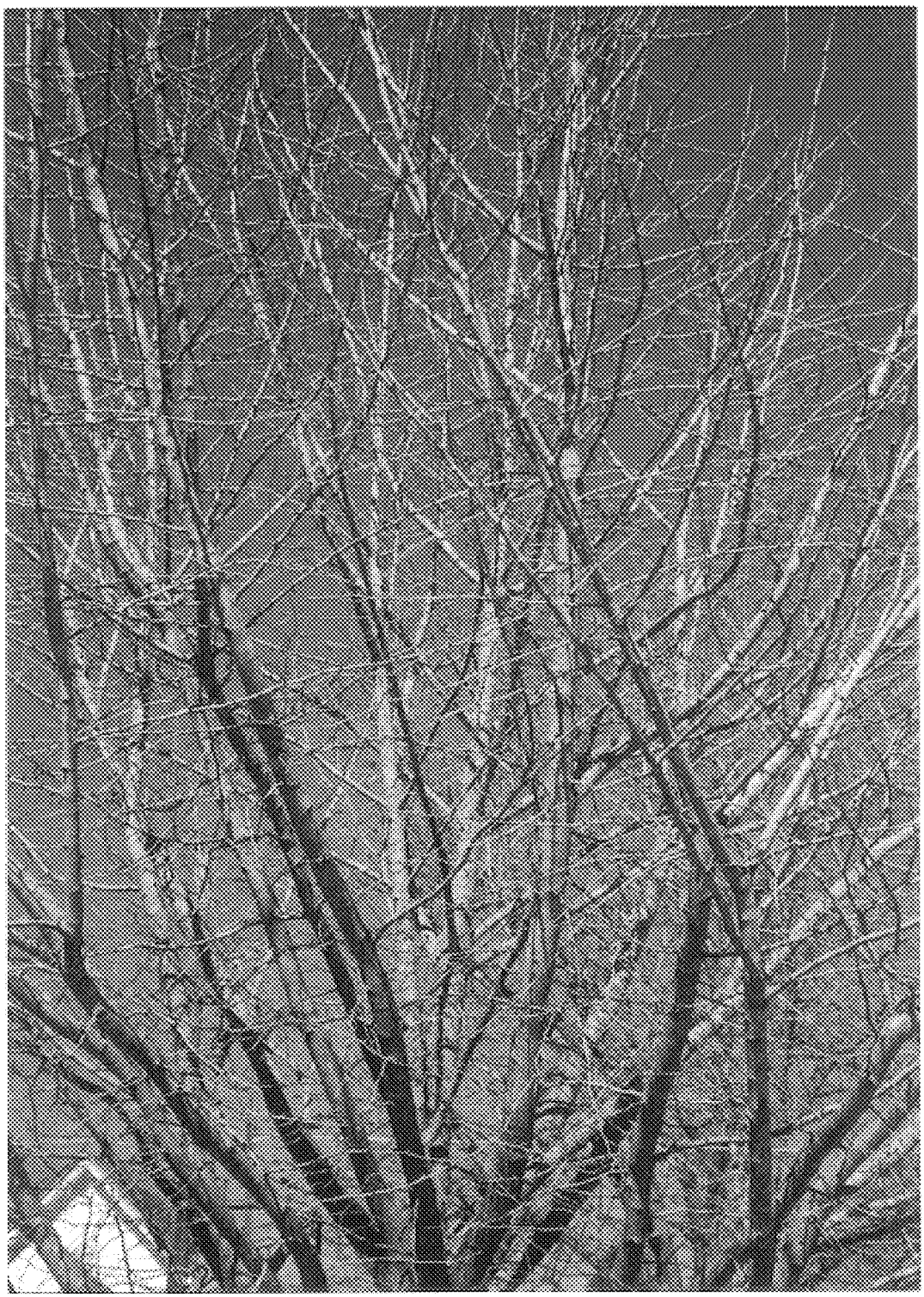

* * * * *